United States Patent
Psaros

(10) Patent No.: US 7,222,622 B2
(45) Date of Patent: May 29, 2007

(54) GAS-DISPENSING DEVICE WITH SELF-CONTAINED GAS CONTAINER HAVING A DIFFUSION MEMBRANE

(75) Inventor: Georgios Psaros, Tullinge (SE)

(73) Assignee: Maquet Critical Care AB, Solna (SE)

( * ) Notice: Subject to any disclaimer, the term of this patent is extended or adjusted under 35 U.S.C. 154(b) by 444 days.

(21) Appl. No.: 10/250,357

(22) PCT Filed: Nov. 15, 2001

(86) PCT No.: PCT/SE01/02540

§ 371 (c)(1),
(2), (4) Date: Jun. 30, 2003

(87) PCT Pub. No.: WO02/055144

PCT Pub. Date: Jul. 18, 2002

(65) Prior Publication Data

US 2004/0040558 A1    Mar. 4, 2004

(30) Foreign Application Priority Data

Jan. 10, 2001   (SE) .................................... 0100065

(51) Int. Cl.
*A61M 16/00* (2006.01)
*A62B 7/00* (2006.01)

(52) U.S. Cl. .................... 128/204.18; 128/200.24; 128/203.12; 128/205.11

(58) Field of Classification Search ........... 128/200.25, 128/200.29, 203.12, 203.14, 203.25, 205.27, 128/205.11, 200.24, 204.18, 205.22; 222/187, 222/189.06

See application file for complete search history.

(56) References Cited

U.S. PATENT DOCUMENTS

| 3,634,053 A | | 1/1972 | Klass |
| 3,833,116 A | | 9/1974 | Lucero et al. |
| 4,552,555 A | | 11/1985 | Theeuwes |
| 5,845,633 A | * | 12/1998 | Psaros .................... 128/200.24 |
| 6,070,577 A | * | 6/2000 | Troup .................... 128/205.22 |
| 6,484,720 B1 | * | 11/2002 | Marquard et al. ..... 128/205.24 |

FOREIGN PATENT DOCUMENTS

| EP | 0 783 896 | | 7/1997 |
| EP | 0 806 216 | | 11/1997 |
| EP | 0806216 A1 | * | 11/1997 |

* cited by examiner

Primary Examiner—Justine R. Yu
Assistant Examiner—Amadeus Lopez
(74) Attorney, Agent, or Firm—Schiff Hardin LLP

(57) ABSTRACT

A gas-dispensing device (2) for dispensing a gas into breathing gas, comprising a membrane (6) through which the gas can diffuse into the breating gas, is described. The gas-dispensing device (2) is simple and reliable because it contains a self-contained chamber (4) in which the gas is held at a predefined overpressure, and the membrane (6) is arranged to form a part of the chamber's (4) wall.

8 Claims, 2 Drawing Sheets

GAS-DISPENSING DEVICE WITH SELF-CONTAINED GAS CONTAINER HAVING A DIFFUSION MEMBRANE

BACKGROUND OF THE INVENTION

1. Field of the Invention

The present invention is directed to a gas-dispensing device for dispensing a gas into a breathing gas, of the type having a membrane through which the gas can diffuse into the breathing gas. The invention also is directed to a breathing apparatus having such a gas-dispensing device.

2. Description of the Prior Art

In conjunction with respiratory care (with a respirator, ventilator, anesthetic machine or other breathing machine), the physician may sometimes wish to supplement the breathing gas with a medical gas. NO is an example of a medical gas, but there are other gases with a therapeutic or other effect (e.g. anesthetic, analgesic).

One way to dispense a gas is to utilize a membrane permeable to the gas. The rate of diffusion then governs the amount dispensed. Connecting a gas source containing the gas to be dispensed into the flow of breathing gas in a breathing apparatus via a membrane is known.

One disadvantage of this system is that the gas source may be bulky. Patient transport then becomes more difficult, or dispensing may need to be interrupted during transport. The gas source can also require more rigorous safety precautions to ensure that the gas source does not leak. This is the case for e.g. NO and anesthetic gases. In addition, the gas-dispensing system must be equipped to prevent overdosing, even if the membrane or some other component (e.g. a pressure regulator) should fail.

Another disadvantage of known techniques is that special monitoring equipment, or special pressures combined with fixed valves etc., are required if a specific total amount (a given amount of gas) is to be dispensed.

SUMMARY OF THE INVENTION

An object of the present invention is to provide a gas-dispensing device that eliminates, at least in part, the problems associated with gas-dispensing devices according to the prior art.

Another objective is to provide a breathing apparatus, which allows the dispensing of a gas into breathing gas in a simple and uncomplicated fashion that is still safe and accurate.

The first object is achieved in accordance with the invention in a gas-dispensing device having a membrane through which gas can diffuse into breathing gas, and having a self-contained chamber in which the gas to be dispensed is contained at a predetermined overpressure, with the membrane forming a part of the wall of the self-contained chamber.

Instead of a procedure in which a source of gas is connected to a dosing means, a self-contained chamber is charged with a specific amount of gas to be dispensed. This is accomplished by filling the chamber with gas at a specific overpressure and closing it. The chamber also contains a membrane through which the gas diffuses. When the chamber is placed in the flow paths of a breathing apparatus (or when at least the membrane is placed in contact with the flow paths), the enclosed gas is continuously dispensed. Since the diffusion is mainly governed by the partial pressure difference on both sides of the membrane, the overpressure need not be particularly large.

Gas dispensing can be suitably regulated by covering the membrane with a covering means (preventing leakage before use) that can be removed to differing extents. This exposes the membrane to varying degrees, and the amount dispensed can thereby be varied. The total amount dispensed can never exceed the amount held in the chamber.

Pressure in the gas-dispensing device drops as gas diffuses out, thereby causing a drop in the amount dispensed. The rate of decline is virtually linear. This could be an advantage in some situations. Some gases need to be dispensed in large quantities initially but in gradually declining amounts thereafter until no more gas is dispensed. This kind of control was previously hard to achieve and demanded constant resetting of valves or other control components. With the gas-dispensing device according to the invention, dispensing gas in declining amounts is automatic.

When dispensing needs to be more uniform over a longer period of time, an increasingly large area of the membrane can be uncovered at certain intervals. A large exposed area leads to large diffusion that compensates for drops in pressure. However, this does produce some variation in the amount of gas being dispensed.

A more uniform dispensing of gas is provided when the chamber contains a donor substance for the gas. The donor substance could be a liquid (e.g. anesthetic liquid) or a solid (e.g. an NO donor material). As long as there is a donor substance present (or as long as the donor substance provides the gas), a partial pressure will be sustained.

In order to achieve completely uniform gas dispensing, it is advantageous for the gas-dispensing device to have a pressure device that maintains pressure inside the chamber. One such pressure device can be e.g. a spring-loaded piston that compresses the gas.

This could also be done when there is a donor substance present in the chamber.

Pressure in the dosage container can be measured with a pressure gauge. The pressure gauge can advantageously be battery-powered.

It would be advantageous during long periods of gas dispensing if the gas-dispensing device were to be equipped with a refill device, particularly when the gas-dispensing device is incorporated into or a fixed part of the breathing apparatus.

The refill device can be adapted for refill of gas and/or donor substance.

The second object is achieved in accordance with the invention in a breathing apparatus for supplying breathing gas to a patient having a gas-dispensing device of the type described above.

Depending on the application, having a separate gas-dispensing device placed in the flow paths may sometimes be unsuitable. The breathing apparatus could then be suitably devised so the gas-dispensing device is a fixed, integral part of the breathing apparatus.

Integrating the gas-dispensing device with a tracheal tube or inspiratory line would then be particularly advantageous.

DESCRIPTION OF THE PREFERRED EMBODIMENTS

Figure 1:
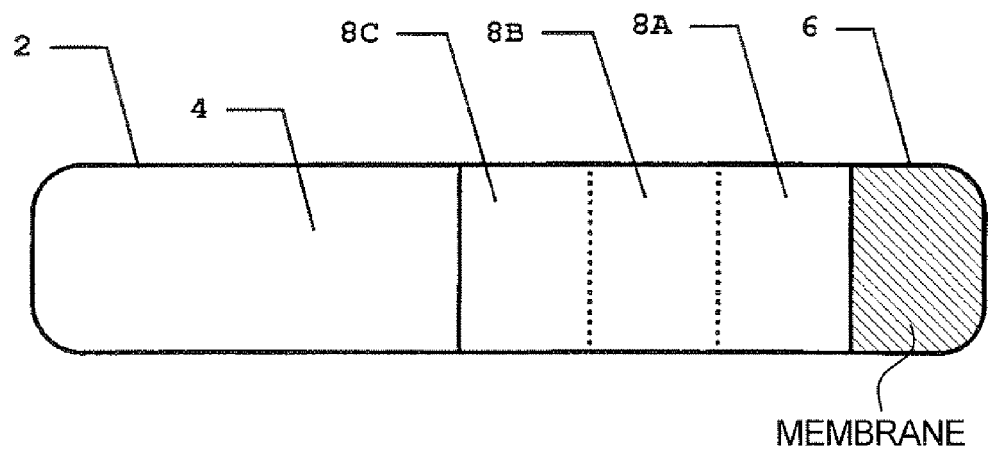
FIG. 1 illustrates a first embodiment of a gas-dispensing device according to the invention.

FIG. 1 shows a first embodiment of a gas-dispensing device 2 according to the invention. The gas-dispensing device 2 has a closed chamber 4 holding a gas, at a predefined overpressure, to be dispensed. A membrane 6 is arranged at one end of the chamber 4. The membrane 6 can occupy a smaller or larger part of the chamber 4. Gas inside the chamber 4 diffuses out into atmosphere when the membrane 6 is uncovered. When the gas-dispensing device 2 is placed in the flow paths of a breathing apparatus, the gas can be dispensed into a breathing gas. A covering means covers the membrane 6 before the membrane is put into use. This prevents leakage of gas before dispensing is to take place.

FIG. 1 shows how the covering means can be formed by different segments 8A-C removed, one at a time (one segment has already been removed to show the membrane), from the chamber 4. The magnitude of the dispensed dose can be selected by exposing the membrane to differing degrees. For example, exposure of a small area of the membrane 6 can be selected for neonates, a somewhat larger area for infants etc. up to the largest area for adults.

Pressure (the partial pressure of the gas) in the gas-dispensing device 2 drops as the gas diffuses out through the membrane 6. This leads, in turn, to a drop in the amount of gas dispensed. This is an advantage with some gases, since it leads to gentler tapering off of medication. However, more uniform dispensing is desirable with other gases. One way to maintain the amount of gas dispensed is to increase the area of exposed membrane 6 by removing more segments 8A-C.

Figure 2:
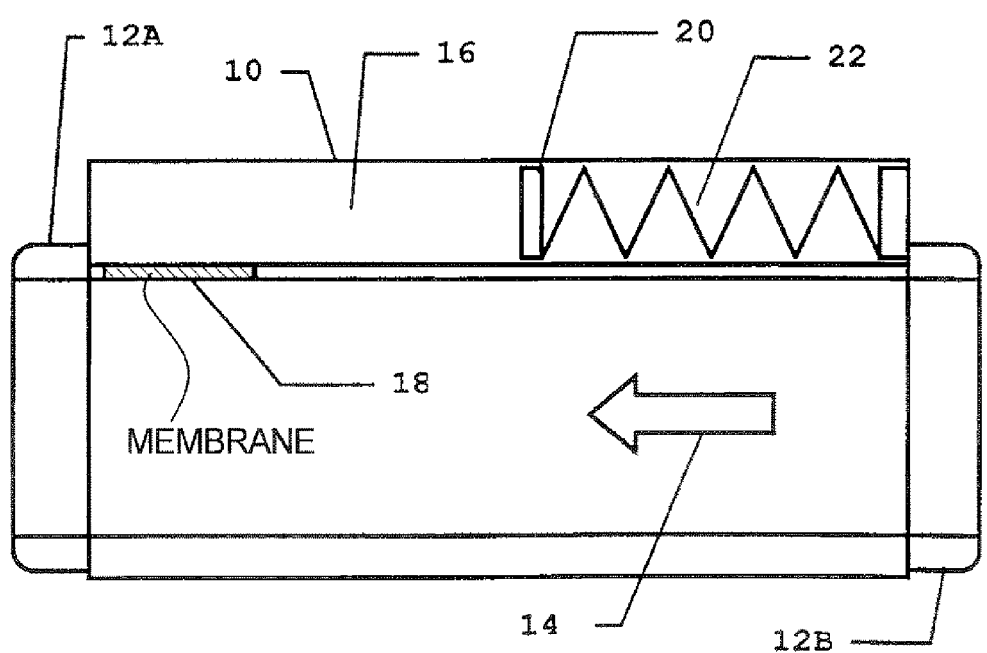
FIG. 2 illustrates a second embodiment of a gas-dispensing device according to the invention.

FIG. 2 shows a second embodiment of a gas-dispensing device 10. The gas-dispensing device 10 can be connected to a system of tubing on a breathing apparatus via a first connection end 12A and a second connection end 12B. Breathing gas can flow e.g. as designated by the arrow 14.

The gas to be dispensed is in a chamber 16 and is dispensed into the flow of breathing gas 14 via a membrane 18.

A small piston 20 is arranged to compress the gas so as to keep gas dispensing as constant as possible over time. In this instance, the piston 20 is driven by a spring 22. Relatively constant gas dispensing can be achieved, as long as any gas is left in the chamber 16, by the choice of dimensions for the chamber 16 and the piston 20 and the type of spring 22.

Figure 3:
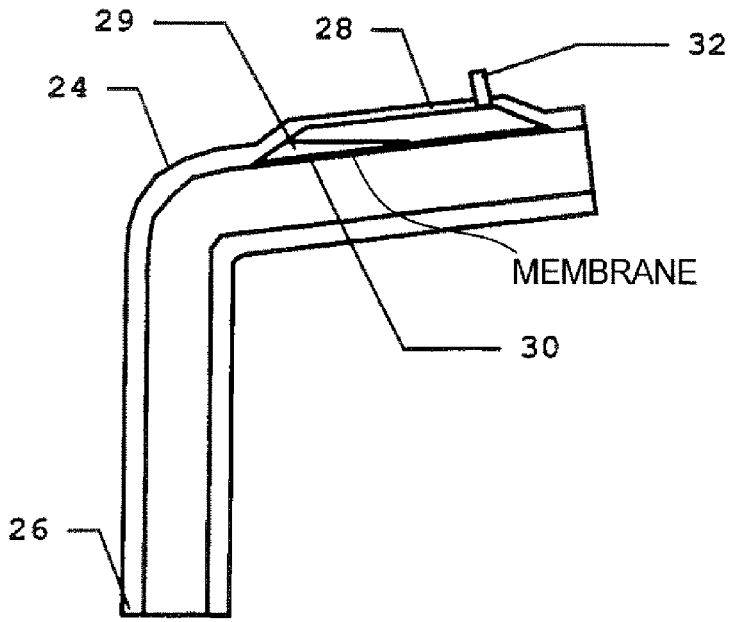
FIG. 3 illustrates a third embodiment of a gas-dispensing device according to the invention.

FIG. 3 shows a third embodiment of the gas-dispensing device according to the invention, in the form of a tracheal tube 24 in this instance. The tracheal tube 24 has an end 26 devised for insertion into a patient's airways. Gas in a chamber 28 is dispensed via a membrane 30 into the breathing gas flowing through the tracheal tube 24. The partial pressure of the gas is maintained for a prolonged time by providing the chamber 28 with a donor substance 29 for the gas. The donor substance could be a liquid or a solid. As long as the donor substance can provide the gas, an essentially constant dosing of the gas is maintained.

The chamber can be refilled with fresh gas and/or donor substance via a refill nipple 32 when necessary.

Figure 4:
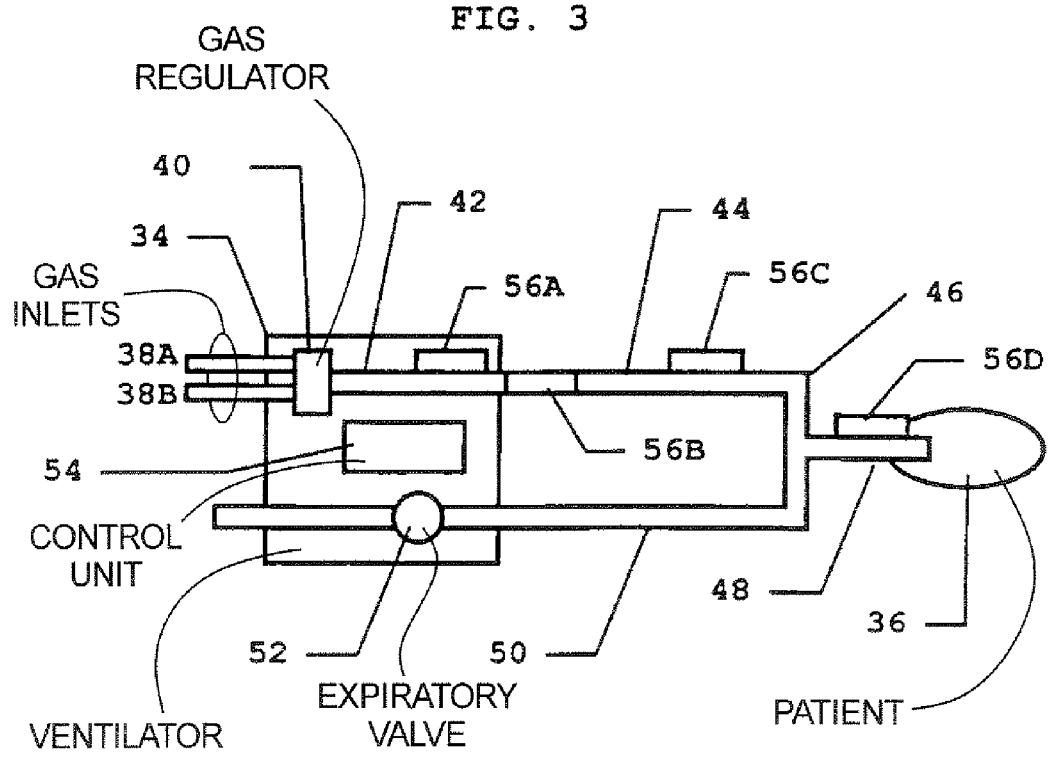
FIG. 4 is a schematic illustration of a breathing apparatus according to the invention, indicating locations at which a gas-dispensing device according to the invention can be located or incorporated.

FIG. 4 shows one embodiment of a breathing apparatus, in the form of a ventilator 34, according to the invention.

The ventilator 34 can be connected to a patient 36 in order to supply her/him with breathing gas. The breathing gas can consist of one or more gas components. FIG. 4 depicts the ventilator 34 with a first gas inlet 38A and a second gas inlet 38B to illustrate this. The gases are mixed in the correct proportions and quantities in a gas regulator 40. The breathing gas then flows through an inspiratory channel 42 to an inspiratory line 44. The inspiratory line 44 is connected to a 3-way connector 46. The 3-way connector 46 is connected to a tracheal tube 48 and to an expiratory line 50. The expiratory line 50 carries breathing gas from the patient, via an expiratory valve 52, to atmosphere or an evacuation (not shown). A control unit 54 controls the ventilator. Other common components in the ventilator 34, such as pressure and flow gauges, are not shown in FIG. 4 because they are well known.

A number of examples of where the gas-dispensing device can be placed or made an integral part of the ventilator 34 is shown for the ventilator 34.

Here, a first gas-dispensing device 56A is shown in the inspiratory channel 42, a second gas-dispensing device 56B is shown connected to the inspiratory line 44, a third gas-dispensing device 56C is shown connected to the inspiratory line 44 and a fourth gas-dispensing device 56D is shown connected to a tracheal tube 48. The second and fourth gas-dispensing devices 56B, 56D can be the gas-dispensing devices shown in FIG. 2 and FIG. 3 respectively.

Combinations of the depicted embodiments are fully feasible. Thus, all the gas-dispensing devices can be equipped with one or more segments according to FIG. 1, a piston and spring according to FIG. 2, donor substance and a refill nipple according to FIG. 3.

In a similar fashion, the gas-dispensing device according to the invention can be used with respirators, anesthetic machines, sub-acute devices (e.g. for home nursing) etc.

Although modifications and changes may be suggested by those skilled in the art, it is the invention of the inventor to embody within the patent warranted heron all changes and modifications as reasonably and properly come within the scope of his contribution to the art.

The invention claimed is:

1. A gas dispensing device for dispensing a gas into a breathing gas, comprising:
    a self-contained chamber charged with a gas to be dispensed and sealed to maintain said gas at a predetermined overpressure; and
    a membrane through which said gas can diffuse into breathing gas due to said overpressure, said membrane forming a part of a wall of said self-contained chamber and, after charging of said self-contained chamber with said gas to be dispensed, said self-contained chamber having no ingress or egress for said gas other than said membrane; and
    a pressure device for maintaining pressure in said chamber during dispensing of said gas.

2. A gas dispensing device as claimed in claim 1 comprising a cover for said membrane, allowing said gas to be dispensed only upon removal of said cover.

3. A gas-dispensing device as claimed in claim 2 wherein said cover is variable in size, to selectively cover different portions of said membrane to selectively set an amount of said gas dispensed through said membrane.

4. A gas-dispensing device as claimed in claim 1 wherein said chamber contains a donor substance in said gas.

5. A gas dispensing device as claimed in claim 1 further comprising a refill arrangement in communication with said chamber allowing said chamber to be refilled.

6. A breathing apparatus comprising:
a source of breathing gas; and
a gas dispensing device disposed to interact with said source of breathing gas, said gas dispensing device comprising a self-contained chamber charged with a gas to be dispensed and sealed to maintain said gas at a predetermined overpressure, and a membrane through which said gas can diffuse into breathing gas, said membrane forming a part of a wall of said self-contained chamber and, after charging of said self-contained chamber with said gas to be dispensed, said self-contained chamber having no ingress or egress for said gas other than said membrane; and
a pressure device for maintaining pressure in said chamber during dispensing of said gas.

7. A breathing apparatus as claimed in claim 6 comprising an inspiratory passage, and wherein said gas dispensing device is disposed in said inspiratory passage.

8. A breathing apparatus as claimed in claim 6 comprising a patient connector, and wherein said gas dispensing device is disposed in said patient connector.

* * * * *